(12) United States Patent
Iuliano (10) Patent No.: US 7,304,722 B2
(45) Date of Patent: Dec. 4, 2007

(54) APPARATUS FOR PERFORMING TWIN ENTANGLED CO-INCIDENT PHOTON ENHANCED RAMAN SPECTROSCOPY AND AN INSPECTION APPARATUS USING THE SAME

(75) Inventor: Michael J. Iuliano, Point Pleasant Beach, NJ (US)

(73) Assignee: In Technology Holdings LLC, Toms River, NJ (US)

( * ) Notice: Subject to any disclaimer, the term of this patent is extended or adjusted under 35 U.S.C. 154(b) by 248 days.

(21) Appl. No.: 11/032,338

(22) Filed: Jan. 10, 2005

(65) Prior Publication Data

US 2006/0152719 A1    Jul. 13, 2006

(51) Int. Cl.
*G01J 3/44* (2006.01)
(52) U.S. Cl. .................. 356/72; 356/301; 356/364
(58) Field of Classification Search ............. 356/301, 356/72; 378/70
See application file for complete search history.

(56) References Cited

U.S. PATENT DOCUMENTS

| | | | |
|---|---|---|---|
| 6,822,739 B2* | 11/2004 | Sergienko et al. | 356/369 |
| 2003/0098979 A1* | 5/2003 | Dress et al. | 356/484 |
| 2005/0243324 A1* | 11/2005 | Freeling et al. | 356/450 |
| 2005/0288564 A1* | 12/2005 | Iuliano | 600/318 |

* cited by examiner

*Primary Examiner*—Gregory J. Toatley, Jr.
*Assistant Examiner*—Kara E Geisel
(74) *Attorney, Agent, or Firm*—Gottlieb, Rackman & Reisman, P.C.

(57) ABSTRACT

A method and apparatus to perform non-invasive molecular detection and analysis are disclosed. The apparatus incorporates co-incident biphotons as the Raman backscattering excitation source and the detection and analysis of the resulting backscatter characteristics is performed through quantum state transfer between entangled biphotons, as well as conventional means.

20 Claims, 9 Drawing Sheets

APPARATUS FOR PERFORMING TWIN ENTANGLED CO-INCIDENT PHOTON ENHANCED RAMAN SPECTROSCOPY AND AN INSPECTION APPARATUS USING THE SAME

RELATED APPLICATIONS

This application is related to the following applications, incorporated herein by reference:

Co-incident Photon Enhanced Stimulated Raman Spectroscopy of In-Vivo Analytes. (Ser. No. 10/872,033) and Method and Apparatus for detecting Chemical & Biological weapon components using Co-incident Photon Enhanced Stimulated Raman Spectroscopy (Ser. No. 10/872,032).

BACKGROUND OF THE INVENTION

1. Field of Invention

The present invention describes a new and unique technique in which the Raman effect is amplified through the use of co-incident entangled biphotons and the resulting Raman signature is captured by quantum state transfer between entangled biphotons. The geometry of the system is selected to produce two monochromatic, coherent, polarized, quantum state entangled, exclusively or nearly exclusive co-incident photons beams through Spontaneous Parametric Downconversion (SPDC). One beam, the probe beam, is directed at the sample or target, while the other beam, the detector beam, is directed at a remote quantum state characteristic detector. Both the resultant conventional Raman backscatter spectrum and the changes in the quantum state characteristics of the entangled biphotons are analyzed to determine the sample's composition.

2. Background of the Invention

Raman effect involves the way in which light scatters off any surface. That is to say, when light of any wavelength impinges on a surface (or molecule), most of the scattered photons are elastically (or Rayleigh) scattered. That means that they leave with the same frequency (or wavelength) as the incident radiation. However, a small fraction of the scattered light (less than one in a thousand incident photons) is inelastically (or Raman) scattered at frequencies that differ from the incident frequency by a value determined by the molecular vibrations of the sample. This process can be thought of as being similar to a Two Photon Absorption (TPA) event. That is, in order for Raman scattering to occur two photons must strike a molecule at the same time. But unlike TPA, one of the photons is absorbed while the other is simultaneously re-emitted at a different frequency by either gaining or losing some energy from the molecule's vibrational energy state. In other words, Raman scattering creates a discrete molecular spectrum at frequencies corresponding to the incident frequency plus or minus the molecular vibrational/rotational frequency. A Raman spectrum is thus a plot of the intensity of scattered light as a function of frequency (or wavelength). By convention, Raman spectra are presented graphically with the wave numbers (reciprocal centimeters) along the horizontal axis and the abscissa representing intensity or energy.

Raman spectra have long been used to determine the structure of inorganic and biological molecules, including the composition of complex multi-component samples. Raman spectroscopy is considered to have many advantages as an analytical technique. Most strikingly, it provides vibrational spectra that act as a molecular fingerprint containing, unique, highly reproducible, detailed features, thereby providing the possibility of extremely selective molecular determinations.

As compared to other forms of analysis, the Raman approach is advantageous for several reasons:
1. Solid, liquid and gas states can be analyzed
2. Aqueous solutions present no special problems
3. No special pre-scanning preparation of the sample is necessary
4. The low frequency region is easily obtained
5. The device can be made inexpensive lightweight and portable
6. Scanning can be completely non invasive and non destructive
7. Scanning distance can be varied from millimeters to kilometers As discussed above, it is well known that conventional Raman scattering relies on the simultaneous, random coincidence of 2 photons striking a sample to produce a Raman frequency shift. Since lasers produce high-density photon populations they greatly increase the chance of random simultaneous photon strikes. This in turn greatly improves the Raman signal intensity. But even with this improvement, it is still a major challenge for all of the Raman techniques to date to collect spectral information with sufficiently high signal-to-noise ratios to discriminate weak analyte signals from the intertwined background noise. This is especially true if it has to be done quickly and nondestructively.

Due to the incredible potential of Raman scattering as a tool for high-resolution molecular or chemical analysis prior inventors have developed various Raman scattering techniques. Each in their own way have improved upon the conventional Raman backscattering technique through amplification of the signal production, improved the signal detection or improved signal analysis. These techniques include:

Dispersive Raman: This is a technique where the Raman backscatter is processed through a optical grating to separate out each individual frequency peaks which are then simultaneously analyzed.

Fourier Transform (FT-R): This is a technique where the Raman backscatter signal is collected as a composite of frequency peaks. This composite spectrum is processed through a Fourier Transform algorithm to yield each individual frequency peak.

Resonance Raman (RR): Resonance Raman scattering occurs when the photon energy of the exciting laser beam matches that of an electronic transition of a chromophoric group within the system under study. Under these conditions bands belonging to the chromophore are selectively enhanced by factors of $10^3$ to $10^5$.

Coherent Anti-Stokes Raman Spectrum (CARS): This is a technique where the Raman backscatter signal is amplified by illuminating the specimen under investigation by two monochromatic light fields, called pump- and Stokes-signal. Similar to RR, their frequency difference is tuned to a Raman-active transition of the chemical compound of interest.

Surface Enhanced Raman Spectroscopy (SERS): Is a technique where Raman backscattering intensity of a sample is significantly enhanced when the target molecules are absorbed onto an electrochemically roughened surface.

Surface Enhanced Resonant Raman Spectroscopy (SERRS): This technique is the same as SERS except the frequency used for excitation of the sample is that of an electronic transition of a chromophoric group within the system under study.

Fourier Transform Surface Enhanced Raman Spectroscopy (FT-SERS): This is the same technique as SERS except the signal analysis is processed through a Fourier Transform algorithm.

Each of the above conventional techniques has been developed in an attempt to overcome the notorious low quantum efficiency of Raman scattering. In other words, very few inelastic scattering events occur in comparison to the number of elastic scattering events. Conventionally, in non-resonance Raman spectroscopy in order to double the efficiency of Raman scattering it is necessary to square the photon density. Unfortunately this can damage the sample. Therefore it is necessary to perform scans at either long integration times or high power densities to achieve acceptable signal-to-noise ratios.

The other forms of Raman scattering like, resonance and surface enhancement or the combination of both can significantly improve the sensitivity and selectivity of Raman measurements. However, these enhancements are not generally applicable to all analytes or to all samples.

All of the above techniques rely on excitation with conventional lasers and measure the reflected backscatter through convention detection. The embodiment of this invention intends to improve and extend each of these techniques by using twin entangled co-incident biphotons as the Raman backscattering excitation source. It also intends to measure the resultant Raman effect via detection and analysis of the backscatter characteristics through quantum state transfer between entangled biphotons as well as by conventional means.

Although not devised for Raman backscattering, previous inventors have recognized the potential for using twin biphotons for improving the signal production when scanning of objects. U.S. Pat. No. 5,796,477 discloses an "entangled-biphoton" microscope, for WF fluorescence microscopy.

SUMMARY OF THE INVENTION

Briefly, the present invention generally describes a truly new and unique technique where the Raman effect is amplified through the use of co-incident quantum entangled biphotons and the resulting Raman signature is captured by quantum state transfer between entangled biphotons. More specifically, the invention pertains to a system and method which intends to improve and extend Raman Spectroscopy techniques by:

1. Using twin entangled co-incident photons as the Raman backscattering excitation source;
2. Detection and analysis of the backscatter characteristics through quantum state transfer between entangled photons as well as through conventional means.

A feature of this invention is that it uses two counter intuitive phenomena in quantum mechanics called superposition and non-locality. Superposition is the sharing of a single temporal and spatial state. This allows for example two photons two exist in the same spot at the same time. (This is very advantageous when you want to create a TPA event or TPA-like event). Non locality on the other hand is a characteristic where separate photons can share a single quantum state. This is allows, for example, two quantum entangled photons to undergo the exact same state change. The interesting part is that they both can share this "single" state even though they are separated by a great distance. (This is very advantageous if you want to look at an event remotely).

In essence this invention is a Raman spectrometer that has been modified to significantly amplify Raman backscatter and to remotely detect the change in the quantum state characteristics occurring in the Raman backscatter. The implication of this is that objects scanned at a distance do not need to be near a detector. This allows for in situ analysis of distant targets while keeping the power density of the scanning beam very low.

The overall technique is accomplished by processing a laser beam through spontaneous parametric downconversion then setting the optical path geometry to create two separate beams consisting of two coincident biphotons each of which share quantum entangled state with their biphoton twin in the other beam. One set of coincident biphotons, designated the probe beam, travels towards a target where one of the two coincident biphotons undergoes absorption and therefore quantum decoupling from its twin in the other beam (designated the detector beam) while its companion coincident biphoton undergoes Raman backscattering and therefore quantum state changes. Due to its continued entanglement with its twin biphoton in the detector beam, the change in quantum state characteristics that occurred from the Raman backscattering will be will "transferred to" or "shared by" the biphoton twin in the detector beam. Since each set of the coincident biphotons have been created in such a manner to carry the same characteristics as its coincident companion, all the detector needs to due is measure their change in relative quantum state between them. This is similar to the method in reference entitled Experimental Demonstration of Single Photon Nonlocality. In that paper they disclosed adding a "local oscillator" from outside the experiment to act as a reference. In this invention the local oscillator or reference biphoton is the biphoton in the coincident pair whose entangled twin got absorbed at the level of the target. Since either coincident biphoton at the level of the target has equal probability of being absorbed or backscattered it becomes just the relative shift in the quantum states between the two coincident photons that reveal the conventional Raman backscatter data. It is also this random absorption-backscattering and the coincident biphoton path geometry of both sets of biphotons that allows indistinguishably to be preserved which maintains entanglement.

In one embodiment of the invention, the Raman excitation source is created through SPDC or other known phenomena to generate pairs of entangled photons.

In one embodiment, the entangled photons are sent along an optical path to cause them to propagate in superposition or coincident.

In one embodiment, one of the entangled coincident beams, probe beam, is directed toward the target and the resulting conventional Raman back scatter is intercepted, collected and analyzed.

In one embodiment, both of the entangled coincident beams are directed toward a sample and the resulting conventional Raman back scatter is intercepted, collected and analyzed.

In one embodiment, one of the entangled coincident beams, the probe beam, is directed toward the target while the other beam, the detector beam, is sent to a remote quantum state characteristic detector. As the probe beam interacts with the target, a quantum state change occurs in the probe beam, as a function of Raman backscatter. This change in quantum state will be "transferred to" or "shared by" the remote detector beam. Polarization detection is a common technique used in Raman spectroscopy. By carefully creating the down converted beams to have their polarization and their frequency or phase to be entangled, the geometry of the system can be set to read, for example, fractional depolarization per specific frequency. It is also possible to measure fractional depolarization per correlated frequency shift in the probe beam to phase shift in the detector beam. In this way the unique finger print vibrational modes of an analyte can be determined. This makes it possible to obtain molecular constituents without actually collecting and analyzing the Raman back scattered photons.

In another embodiment, both the conventional Raman backscatter from the probe beam and the quantum state changes from the detector beam are analyzed and the results are correlated for increased redundancy and accuracy.

In another embodiment, other types of quantum state characteristics are entangled in the probe and detector beams.

Another aspect of this invention is deep penetrating Raman scanning. This will be accomplished by setting the geometry of the optical path to produce 2 sets of twin entangled photons in the X-ray range. Then recombining each at a focal point anywhere from the surface to deep inside the target. This re-co-incidence of the photons will give rise to Raman scattering at the focal point. As discussed above the quantum changes in the entangled Raman backscatter photons will be transferred to the remote detector beam as well as through the target to a conventional detector and then processed into the targets molecular makeup and topographic image. By gradually moving the focal point through the target and sweeping the beam, a complete full thickness chemical determination of the target is possible.

Another aspect of this invention is penetrating Raman scanning utilizing non-ionizing radiation. This will be accomplished by setting the geometry of the optical path to produce two opposing sets of femtosecond pulsed twin entangled photons beams. Each opposing beam will consist of two beams that are 180 degrees out of phase with each other but only 90 degrees out of phase with their respective opposing beam. Each beam will undergo total destructive interference thereby propagating only a node or "null carrier area" that will not interact with matter. Then as the two sets of opposing "node beam pulses" pass through each other inside the target 46, it is presently believed, wave summing of their phases would occur causing a momentary re-emergence of part of both the beams frequency and amplitude. The photon's frequency and amplitude are then able to interact with the vibrational modes of the target, yielding Raman backscatter. This backscatter data is then observed through quantum state transfer.

DETAILED DESCRIPTION OF THE INVENTION

The present invention describes a system and method for performing molecular or chemical analysis through a modified form of Raman Spectroscopy. It is more accurate to say that this is not just Raman backscattering spectroscopy but also a new technique where the Raman effect is captured by quantum transfer between entangled twin photons. This process is more accurately called Raman Quantum State Transfer Spectroscopy (RQST Spectroscopy). This process is accomplished first by creating two beams consisting of sets of twin quantum entangled coincident photons generated through Spontaneous Parametric Downconversion. Then directing one of the beams, the probe beam, at a molecule or a chemical sample and analyzing the resulting conventional Raman backscatter spectrum while simultaneously analyzing the changes in the quantum state characteristics transferred to or by shared by the entangled biphotons in the other remote beam.

One of the most difficult aspects of any spectroscopic technique is separating the desired signal from background noise. This is especially true of Raman backscattering spectroscopy where the quantum efficiency is recognized to be notoriously low. Again, this is due to the fact that the actual backscatter occurs less than one in a thousand incident photons.

As discussed above, there have been many techniques developed to address the quantum efficiency issue in Raman spectroscopy. One of the still unresolved issues is the fact that Raman scattering occurs in 360 degree fashion but conventional backscattering techniques only captures the photons that actually impinge the detector. This means, that even when optimized for backscatter capture, more than 65% of the total backscatter signal is lost.

Generically speaking, each of the prior art in situ techniques attempt to mitigate this loss has been by increasing the excitation source photon density. This approach improves the signal strength by increasing the number of backscatter events that occur within the detector's capture angle. But in all the prior art attempts, relatively high power densities are used that can cause sample damage or destruction. In many instances this is unacceptable. This is certainly the case, for example, when the sample is in situ in a biologically active organism, inside a highly purified pharmaceutical reaction chamber or part of the mission critical architecture of a microchip. The high power density may also induce black body radiation that may further obscure the Raman spectrum.

An intuitive solution would be to attenuate the laser power to the point where the power density is below the sample damage or destruction level. The major drawback with this approach is that the "normal" or intrinsic amount of Raman scattering has very low efficiency and therefore produces a weak signal in the first place. Attenuating the signal further can cause the loss of the Raman spectrum in the background noise because its intensity is directly related to the total number of photons impinging on the sample. Therefore, any reduction in laser power to the sample must be counterbalanced by increasing the acquisition time. This leads to acquisition times that can reach hours per sample versus seconds or minutes. Compounding this problem is that all the while the probe beam is stimulating Raman backscatter it is also causing the production of natural phosphorescence of many chemicals and bio-molecules which interferes and masks the weak Raman backscattering signal and makes it more difficult to distinguish the resultant Raman spectrum.

Again, the other forms of Raman scattering mentioned above like, resonance and surface enhancement or the combination of both can significantly improve the sensitivity and selectivity of Raman measurements. However, these enhancements often require sample preparation and destruction and are not generally applicable to all analytes or to all samples.

Thus there is a need for an apparatus and method of making quick, safe, accurate, and reliable in situ analysis using Raman phenomena.

The present invention provides several solutions to this problem that can be utilized concurrently or independently of each other.

One embodiment of this invention will eliminate the unintentional collection of all forms of unwanted or confounding signals happening at the level of the sample. Fluorescence is a good example of a source of an undesirable signal. In conventional Raman Spectroscopy during the signal collection period, fluorescence spectra of the target molecules can occur at the same peak of that of Raman spectra. The longer the collection period lasts the worse this effect can become, until the peaks of the Raman spectrum have been completely swamped by the fluorescence signal. This problem is avoided in the Quantum State Transfer Detection technique by the use of a remote detector. That is to say, the process of Raman is an event in which a target molecule undergoes a simultaneous strike by two photons. This event happening at $10^{-14}$ seconds, where one of the co-incident photons is absorbed while the other photon "bounces off" with some loss or gain of energy from the vibrational state of the molecule. This change in photon's energy state is the Raman effect that is perceived as a frequency shift. The important fact here is that this frequency change happens to the same incident photon. That is, this photon momentarily exists as a plasma density wave within the electron probability cloud and is then expelled. The frequency shift is dependent on the point of the molecular oscillation cycle at which this expulsion occurs.

The fluorescence process, like Raman, is also a TPA event. But unlike the Raman event of "absorption and bounce off", in fluorescence both photons undergo absorption and then there is a subsequent emission of a new photon (happening at $10^{-9}$ seconds). The absorption of the target set of twin entangled photons decouples their entangled state so that no "transfer" of information can occur. Since only information can "transfer" between entangled biphotons, any phenomena happening at the level of the sample that disrupts this connection can not and will not be "transferred".

This same absorption-decoupling that occurs to both photons in fluorescence will also occur to one of the incident photons involved in the production of the Raman scattering via twin entangled photons. Since one of the entangled biphotons is absorbed, it decouples from its entangled biphoton in the remote beam leaving only the other coincident biphoton undergoing Raman backscattering available for quantum state transfer. It is this very fact that is the bases for this invention. In essence this process makes it possible to observe the effect of every Raman backscattering event not just the ones that occur in the detector's capture angle as in conventional Raman Spectroscopy. This process is also the underlying reason that makes remote "Raman Spectroscopy" possible. It even means that the since both co-incident biphotons in the remote beam can be created to share a quantum states, like, frequency, phase, polarization, etc., remote quantum characteristic detection is possible and the process is even self-referencing.

This is because each set of twin entangled biphotons share the same relative quantum characteristic. When one set of coincident biphotons strike the target, one biphoton undergoes absorption and the other backscattering. The backscattering event will cause a shift in frequency and a change in polarization to that backscattered biphoton. Now, as previously discussed, only the entangled biphoton twin, of the backscattered biphoton, in the remote beam, will "receive" this quantum state change. But instead of changing in exactly the same way, only its entangled quantum characteristics will shift relative its companion coincident biphoton. This is because its companion has been decoupled from its "absorbed" biphoton twin in the target beam. This relative quantum characteristic shift between coincident biphotons can therefore be correlated to the conventional Raman spectrum shift of the backscatter beam. This means that after making multiple relative quantum shift measurements and correlating them to the conventional Raman back scattering event that cause them, an entire Raman spectrum can be created. This in effect negates the need for detectors to be near the target. And unlike conventional Raman spectroscopy 100% of the backscattered photon information will be collected through Quantum transfer. The combination of all of these factors gives rise to a true remote detection system.

As discussed above, other phenomena occurring at the level of the sample, but that do not change the photons' quantum state, like fluorescence, Rayleigh scattering, etc, will not be transferred. This means that the remote detector will only receive Raman scattering data. This is true for any and all forms of confounding signals happening at the level of the sample.

Another major advantage of Raman Quantum State Transfer Spectroscopy (RQSTS), like non-resonate Raman techniques, is that the sample being scanned does not need preparation for analysis. This means that the sample data can be scanned and obtained in situ allowing for direct, real time non-destructive detection and analysis.

Another major advantage of Raman Quantum State Transfer Spectroscopy (RQSTS) over conventional Raman Spectroscopy is its ability to reveal more than just surface components of a target. This can be accomplished by setting the geometry of the optical path to produce two sets of twin entangled photons in the X-ray range. Then recombining at a focal point anywhere from the surface to deep inside the target. This re-co-incidence of the photons will give rise to Raman scattering at the focal point. As discussed above the quantum changes in the entangled Raman backscatter photons will be transferred to the remote detector beam and then processed into the targets molecular makeup. By gradually moving the focal point through the target and sweeping the beam, a complete full thickness chemical determination of the target is possible.

To Recap RQST Spectroscopy:
1. Needs no sample preparation
2. Uses low density entangled co-incident biphotons as excitation source in contrast to conventional Raman that uses high density random photons
3. Eliminates excessive photon density sample damage
4. Eliminates confounding sample signals by transferring only Raman related quantum state changes
5. Significantly amplifies the signal strength by collecting 100% of the Raman backscatter phenomena through quantum state transfer
6. Sample can remain in situ
7. No detector is required at the level of the sample
8. Entire target composition of the target is possible not just the surface
9. Detection and analysis can be done remotely The implication of all this is that it is now possible to complete a low power, remote or even clandestine, in situ, surface and penetrating analysis of any target.

In order to accomplish the above it will be necessary to address several key factor. First is to create a Raman Excitation source that will reduce the power density to which the sample is exposed while increasing the Raman scattering effect. As discussed above, the Raman effect is similar to a Two Photon Absorption event. That is the Raman effect occurs when two photons strike a molecule at the same time. Since all Raman spectrometers rely on the random co-incidence of two photons to cause backscattering the efficiency has been traditionally very low, around $10^{-6}$ events per incident photon. So the real trick of making Raman backscatting efficient is to make sure that every photon in the excitation becomes coincident. Therefore it would be very advantageous to create and use an excitation source that consists substantially of co-incident photons.

Figure 1:
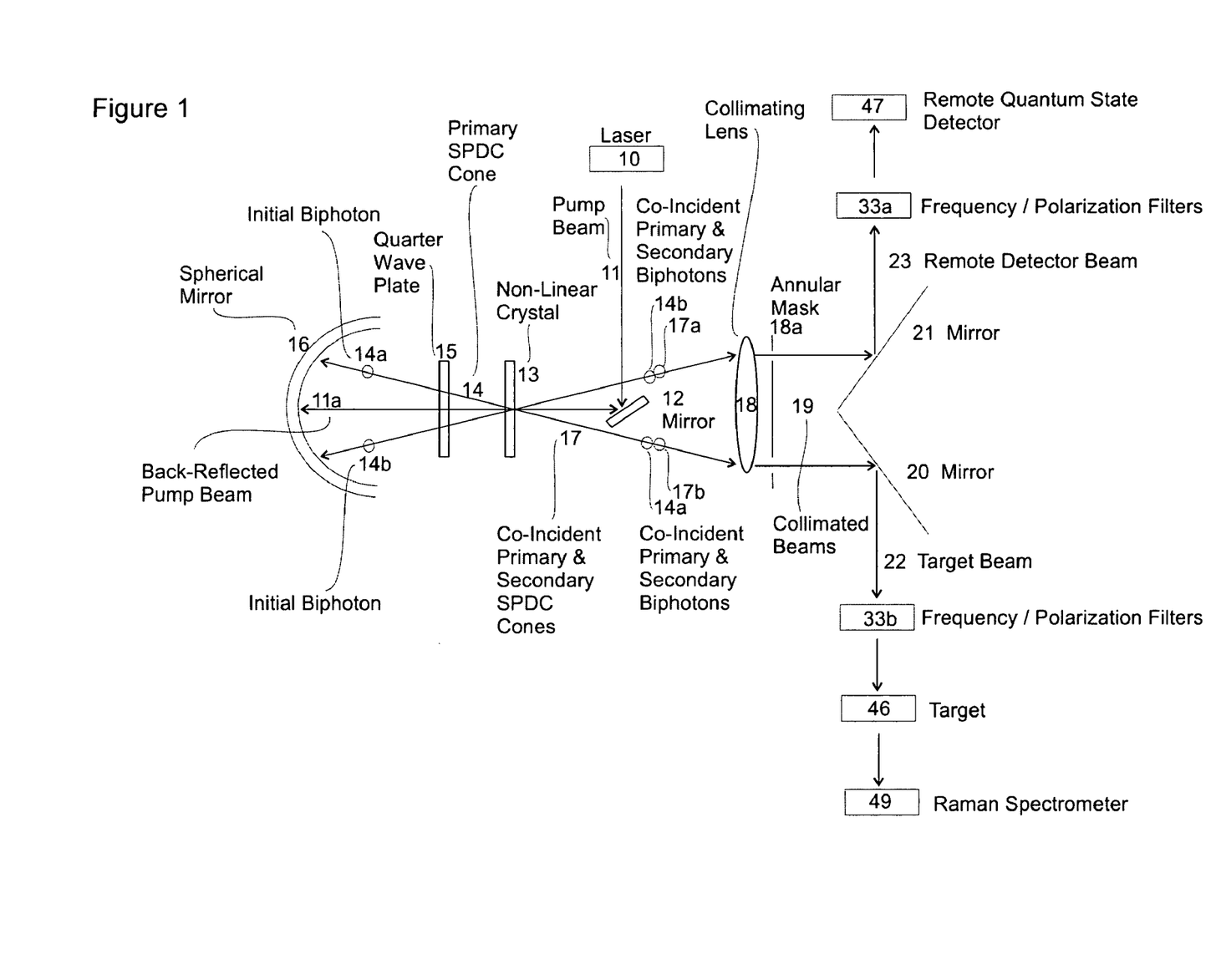
FIG. 1 shows a block diagram of a device used for Coincident Twin Entangled Biphoton Production via co-incident propagation geometry.

FIG. 1 depicts one embodiment of the invention where the twin entangled biphotons are generated in a co-incident manner through know means. (See Ref.: A High Brightness Parametric Source of Entangled Photon States, Laser Physics, Vol. 13, 2003, pp 350-354)

Generally speaking a laser (L) 10 generates a pump beam (PB) 11, which is reflected off a Mirror (M) 12 and through a Non-Linear Crystal (NLC) 13, creating an initial cone of Spontaneous Parametric Downconversion (ISPDC) 14, containing entangled biphotons 14a and 14b. This ISPDC Cone then travels through a Quarter Wave Plate (QWP) 15 to maintain phase and polarization and is reflected by a Spherical Mirror (SM) 16 and back through the QWP 15. At the same time the PB 11 also reflects off the SM 16 as a secondary Pump Beam (SPB) 11a and passes back through the QWP 15 and back through the NLC 13 creating a Secondary SPDC (SSPDC) 17, containing entangled biphotons 17a and 17b. SSPDC 17 is superimposed on the back-reflected initial SPDC 14 and specifically 14b and 17a and also 14a and 17b become coincident. The two coincident SPDC cones then pass through a collimating lens (CL) 18 and Mask (M) 18a which converts them from expanding cones to a Linear Beam (LB) 19. LB 19 consists of now just pairs of coincident entangled biphotons. This beam, 19, can be used in its entirety as the twin entangled biphoton excitation source for conventional Raman Spectroscopy. Alternatively, LB is split in half by mirrors 20 and 21 into a target beam (TB) 22 and a remote detector beam (DB) 23, each containing half of the entangled biphoton pairs. The remote detector beam (RDB) 23 passes through a set of polarizing filters 33a and then enters a remote quantum state detector (RQST) 47. TB 22 passes through a frequency/polarizing filter 33b and then hits the target (T) 46. (Filters 33a and 33b screen out all coincident biphotons pairs that are non-degenerate and not identically polarized.) The backscattered Raman photons from T 46 are intercepted by a Raman spectrometer (RS) 49 that generates a local Raman spectrum.

Figure 2:
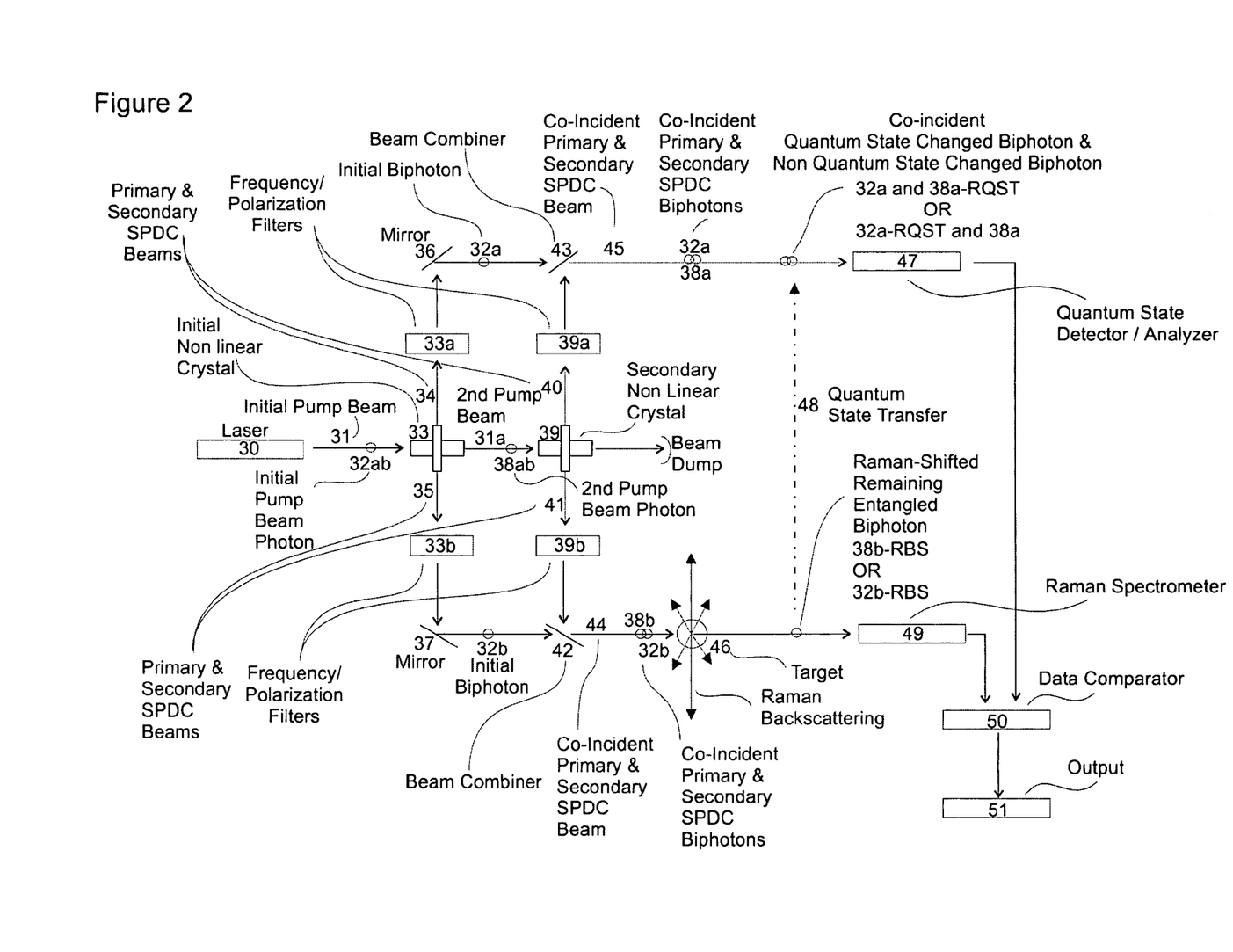
FIG. 2 shows a block diagram of a device used for Coincident Twin Entangled Biphoton Production via counter-propagation geometry.

FIG. 2 depicts one embodiment of the invention where the twin entangled coincident biphotons are generated in a counter-propagating manner. (See Ref.: Controllable frequency entanglement via auto-phase-matched parametric downconversion, Phys. Rev. A, v. 67032307 (2003)). Generally speaking, a Laser (30) generates an initial pump beam (PB) 31, containing photon 32ab, which passes perpendicularly through a single-mode Non Linear Crystal Waveguide (NLWG) 33. Photon 32ab undergoes a Type 1 SPDC into either a degenerate pair of two identically polarized photons 32a and 32b of half the original frequency of 32ab or non-degenerate pair of two identically polarized photons 32a' and 32b' of frequency which sum to that of photon 32ab. These two photons emerge from opposite ends of the NLWG 33 as entangled biphotons beams (EPB) 34 and 35. Photons 34 and 35 then pass through a spectral filter element (SFE) 33a and 33b respectively. These elements screen out all coincident biphotons pairs that are non-degenerate and not identically polarized. These biphotons are subsequently reflected off Mirrors 36 and 37 respectively. The initial PB 31 passes through the initial NLWG 33 to become a secondary pump beam (SPB) 31a. Beam 31a contains photon 38ab. As SPB 31a passes through a secondary NLWG 39, 38ab degenerates into a second set of SPDC biphotons, 38a and 38b in beams 40 and 41 respectively, in the same manner as the initial set. EPB 40 passes through a SFE 39a and is sent on to a Beam Combiner (BC) 43 where biphoton 38a becomes superimposed or co-incident with biphoton 32a from EPB 34 to form the Combined Co-incident beam 1 (CCB1) 45. Beam 45 is the twin entangled biphoton excitation source that can be sent on to the target 46. (In another embodiment of this invention CCB1 will not be sent to the target 46 but on to a remote quantum characteristic detector 47. This aspect is discussed below). Concurrently, the other daughter biphoton, 38b in EPB 41 passes through SFE 33d and is sent on to a Beam Combiner (BC) 42 where it becomes superimposed or co-incident with biphoton, 32b, from EPB 35. This Combined Co-incident Beam 2 (CCB2) 44 is another twin entangled biphoton excitation source that is sent on to the target 46.

As can be seen by the above optical geometry, each set of coincident photons has been frequency, phase and polarization matched. So no matter what frequency pair emerges from the down conversion process, spectral filtering between the two downconversion beams guarantees a companion photon of the same frequency. This allows a relative comparison between each of the biphotons in the coincident pair and their respective quantum states. Furthermore since their path remains unknown, the indistinguishability between the coincident photons is preserved and therefore so is the entanglement.

The upside to the above two techniques is that, if, no spectral filtering is done, both setups will produce a Raman excitation source which is very low in photon density but several orders of magnitude more effective in producing Raman backscattering over that of conventional random laser sources. The downside to the technique is that if one wants to observe the entangled data, spectral filtering will be necessary, which will significantly attenuate the number of available biphotons.

The second issue to address is the fact that Raman Backscattering collection is a notoriously inefficient process. Even the best detectors set directly on top of the target and optimized for collection still only receive about 35% of the actual backscatter. This is because Raman backscatter is produced in a 360-degree sphere while the detector is only able to capture is only a fraction of angle. So the real issue becomes how to capture a larger portion of the Raman backscatter signal.

As discussed above, the generation of co-incident photons through SPDC produces photons that are not only coincident but also are quantum entangled. In other words they share a single quantum state. The significance of this is that if the quantum state changes in one of the entangled biphotons the other entangled biphoton experiences the exact same quantum state change. Therefore, all that is necessary to collect 100% of the Raman Backscatter effect is to superimpose twin sets of entangled biphotons. Then send one half of each set of the twin entangled biphotons towards a target and the other half to a remote quantum state detector. Then as the photons in target beam interacts with the target, they experience a quantum state change, (one photon is absorbed and the other is "re-emitted"), with a new frequency, phase and polarization, as a function of Raman backscatter. This change in quantum state will be "transferred to" or "shared by" one of the twin entangled biphotons remote detector beam. Since frequency, phase and polarization are considered "transferable" quantum states they lend themselves nicely to performing Raman spectroscopy in a remote detection manner. Therefore, by carefully creating the down converted beams to have their polarization, frequency and or phase entangled, the geometry of the system can be set to read, for example, fractional depolarization per specific frequency. This could also be set to read fractional depolarization per correlated frequency phase shift in the probe beam to phase shift in the detector beam. In this way it is then possible to detect the frequency shift peaks of vibrational modes of the target and also determine specific concentration through the depolarization ratio without actually collecting and analyzing any of the conventional Raman back scattered photons.

To summarize, the apparatus of FIG. 2 can be used in one of three configurations. In one configuration, the beams 44 and 45 are combined into a single, high biphoton density beam that is directed at the target 46. The resultant backscattered photons are picked up by a Raman spectrometer 49 that generates a corresponding Raman spectrum. The Raman spectrum is sent to a data comparator 50 which then determines a preselected characteristic of target 46 (for example, whether it contains a specific molecule). The result is then sent to output 51.

In a second configuration PSB 44 impinges on target 46 and the resulting Raman scattered photons are ignored. Meanwhile PSB 45 is sent to a quantum state detector/analyzer 47 that analyzes the relative difference between the entangled quantum state of the coincident biphotons. The quantum analyzer then generates a differential spectrum of the entangled states between the coincident biphotons that yield a characteristic of target 46. This characteristic is sent to the data comparator 50 that then generates a corresponding signal to output 51.

In the third configuration, the results from both the spectrometer 49 and the analyzer 47 are fed to the comparator 50 and analyzed to determine a desired characteristic of target 46. Again the result is fed to output 51.

In all three configurations, the unconverted portion of the $2^{nd}$ pump beam is dumped.

Figure 3:
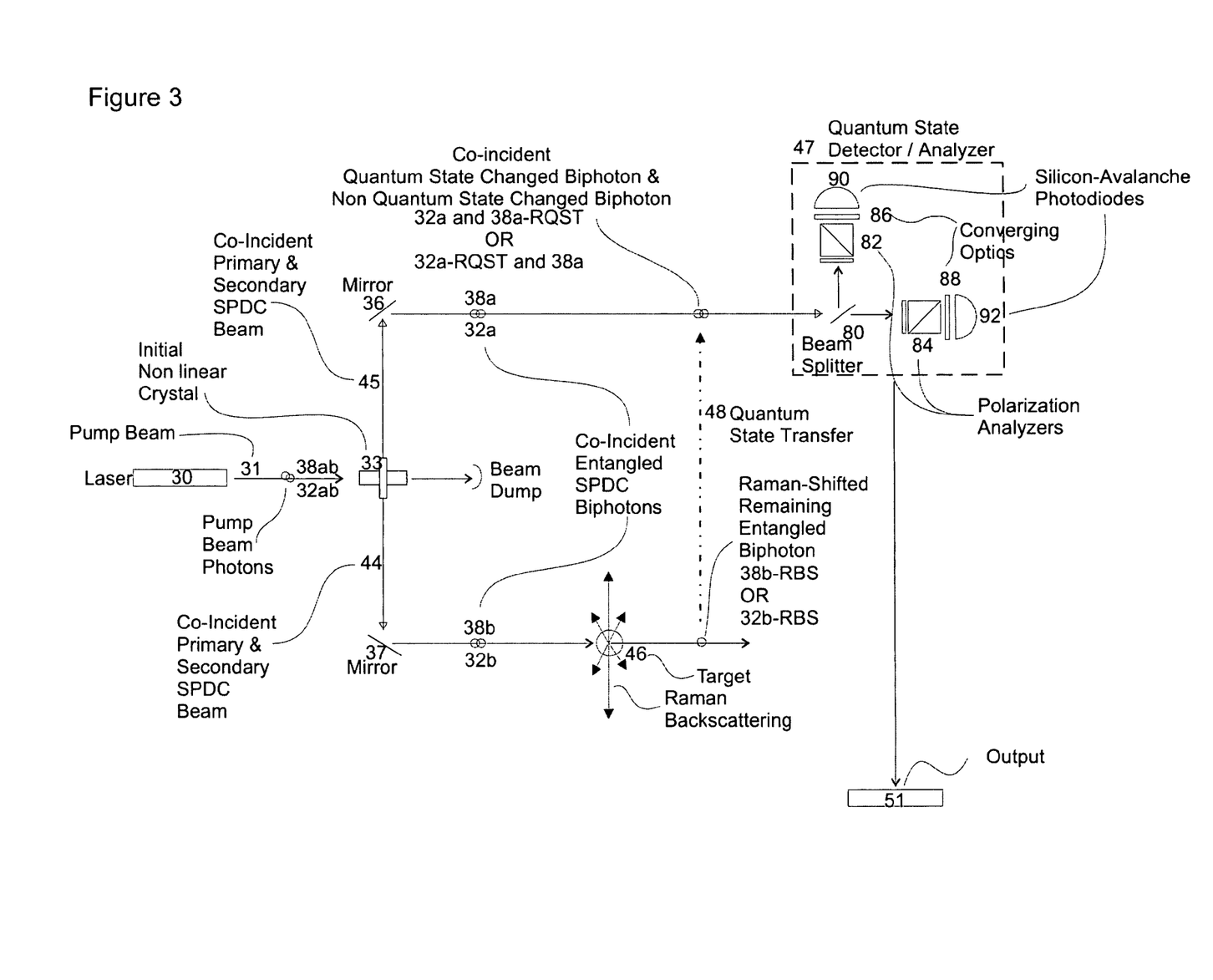
FIG. 3 shows a block diagram of a device for performing Quantum State Transfer Spectroscopy via Twin Coincident Biphoton Enhanced Raman Backscattering.

FIG. 3 depicts the preferred manner for the way in which these measurements can be accomplished. Generally speaking a Laser (30) generates a pump beam (PB) 31, (consisting of either a high frequency laser or a frequency doubled low frequency laser). PB 31 contains photons 32$ab$ and 38$ab$ which passes in a transverse manner (angle of incidence sufficient to cause counter propagation) through a single-mode Non Linear Crystal Waveguide (NLWG) 33, like submicron inhomogeneous periodically poled Lithium Niobate (PPLN) crystal or Surface Periodic Poling in Lithium Niobate (SPPLN). Due to the nature of the (submicron PPLN) NLWG and the angle of incidence, photons 32$ab$ and 38$ab$ undergoes a Type 1 SPDC into a degenerate pair of two counter-propagating, identically polarized photons 32$a$ and 32$b$ and 38$a$ and 38$b$ of half the original frequency of 32$ab$/38$ab$.

That is, biphotons, 32$a$ and 38$a$ propagate in superposition to each other while 32$b$ and 38$b$, also propagate in superposition to each other. But sets 32$a$/38$a$ and 32$b$/38$b$ emerge from the opposite end of the NLWG 33 where they become Combined Co-incident beam 1 (CCB1) 45 and Combined Co-incident beam 2 (CCB1) 44 respectively.

Unlike the FIGS. 1 and 2, there is no need for spectral filters since the submicron inhomogeneous periodically poled Lithium Niobate waveguide will create just degenerate biphotons that are both of identical frequency and polarization. The other important factor in this configuration is that PPLN has the intrinsic properties of creating photons in superposition. This eliminates the needs for multiple downconversion crystals and beam combiners. Thereby greatly reducing the cost and complexity of the invention.

At this point biphoton beams 44 and 45 are sent to the Target 46 and the Remote Detector (RD) 47 respectively. As with many prior experiments that have proved the existence of entanglement, each set of twin biphoton pairs 32$a$ and 32$b$ and 38$a$ and 38$b$ could be set to share the correlated states of frequency and or phase and or polarization. Therefore, simultaneous observation and comparison of coincident pairs, (32$a$/38$b$ and 32$b$/38$a$) will show a high correlation between them. But unlike the experiments that were just looking for the existence of entanglement and properties of non-locality, this invention intends to use the entanglement to transfer information.

The information transferred through entanglement is in the Raman backscattered state. That is, when one of the target beam 44 biphoton, 32$b$ or 38$b$, gets backscattered it shares the state change with its entangled biphoton twin, 32$a$ or 38$a$, respectively. In other words, when beam 44 strikes the target 46, the Raman effect occurs where one of the two coincident twin entangled biphotons either 32$b$ or 38$b$ is absorbed and therefore decoupled from its entangled biphoton in beam 45. This leaves only the remaining entangled biphoton in beam 44 to be backscattered and undergo a quantum state change (frequency shift, phase shift &/or polarization shift). Since this biphoton in beam 44 is still the "same" biphoton it's quantum state will be "transferred" to or "shared" through entanglement 48 with its twin entangled biphoton pair in beam 45 causing a relative frequency, phase and or polarization shift between the two coincident biphotons. This "new" combination of coincident biphotons is designated either as (32$a$ and 38$a$-RQST) or (32$a$-RQST and 38$a$) depending on which biphoton received the Raman quantum state transfer.

As stated above the remote detector 47 receives beam 45 containing biphotons either as (32*a* and 38*a*-RQST) or (32*a*-RQST and 38*a*) depending which biphoton received the Raman quantum state transfer. Here, this pair of biphotons passes through a beam splitter (BS) 80 where they have equal probability of continuing on together or splitting apart. After the BS they enter one or both of two polarization analyzers (PA) 82 and 84 where their polarization state will be analyzed. Following the PAs are lenses 86 and 88 respectively with converging optics that concentrate beam(s) onto one or both single-photon Silicone-Avalanche Photodiodes (SAP) 90 and 92 respectively. The signals from the SAPs are correlated and recorded by a computer.

By measuring the relative shifts in quantum states, frequency phase and polarization, between biphotons (32*a* and 38*a*-RQST) or (32*a*-RQST and 38*a*) in beam 45, the frequency shift that occurred to biphoton 32*b* or 38*b* (now 32*b*-RBS or 38*b*-RBS) is determined. This process is repeated until an entire Raman Spectrum of the target has been generated. These results, like conventional Raman spectroscopy yield the target's chemical makeup and are shown as an output 51.

As mentioned above, the quantum transfer of polarization is also happening from photons in beam 44 to photons in beam 45, as a function quantum state sharing or entanglement 48, during Raman backscattering. So, it is also possible to determine the targets depolarization ratio by measuring the change in polarization of photons 32*a* or 38*a* relative to its non changing companion photon 38*a* or 32*b*. This process is repeated until the entire depolarization profile has been built for each of the "quantum frequency or phase shift to conventional Raman shift peaks" data sets. The depolarization ratio will, like in conventional Raman spectroscopy, yield the targets chemical concentration. The combination of the two techniques will yield the targets chemical make up along with the chemical's concentration.

Figure 4:
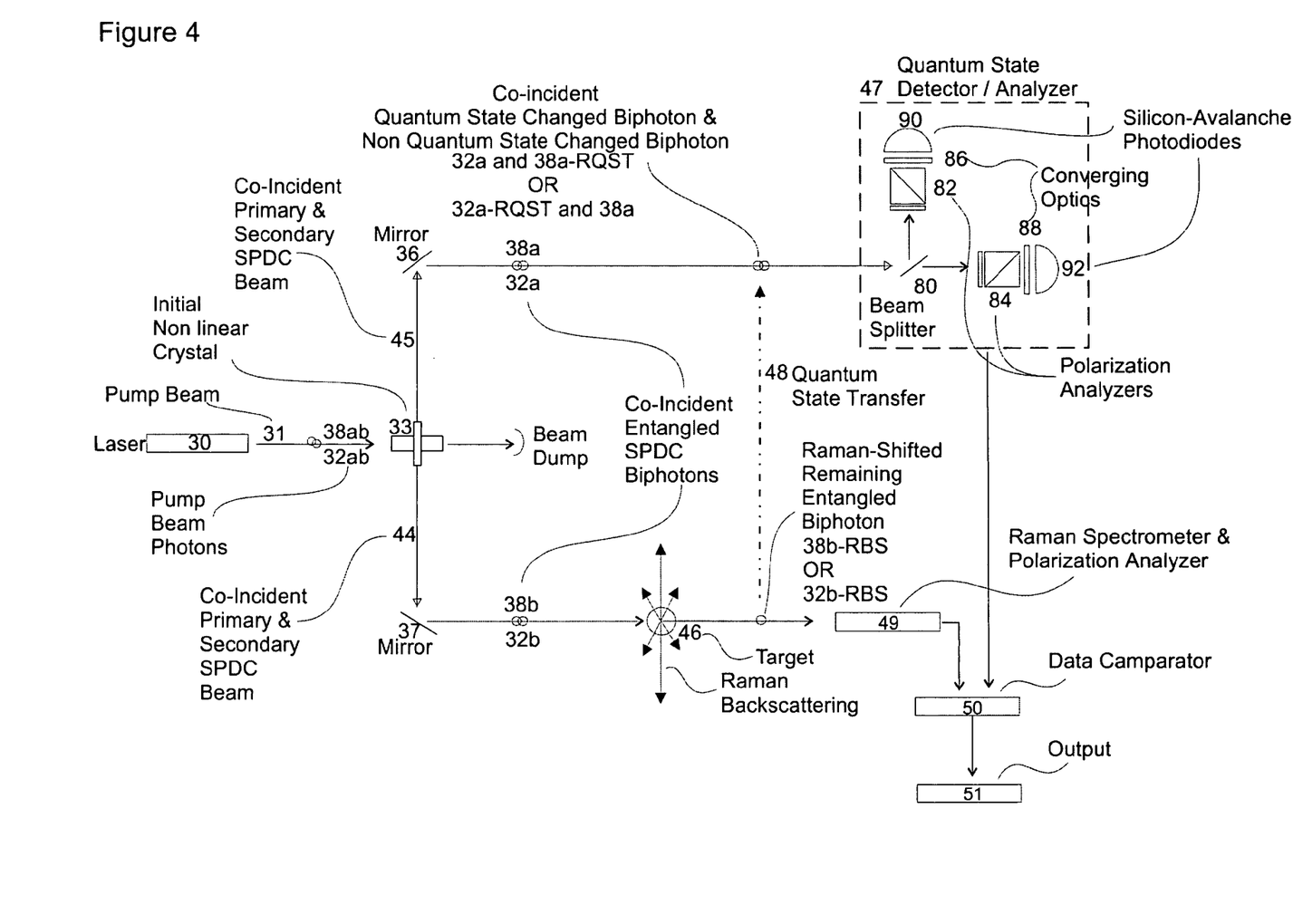
FIG. 4 shows a block diagram of a device for performing Quantum State Transfer Spectroscopy via Twin Coincident Biphoton Enhanced Raman Backscattering with Conventional Raman Spectroscopy.

FIG. 4 is similar to the block diagram of FIG. 3 with the addition of a conventional Raman spectrometer and polarization analyzer 49 at the level of the target to further improve signal detection. Also a data comparator 50, has been added to allow the comparison between conventional spectroscopy results and quantum transfer results. This will improve accuracy and build in redundancy.

Figure 5:
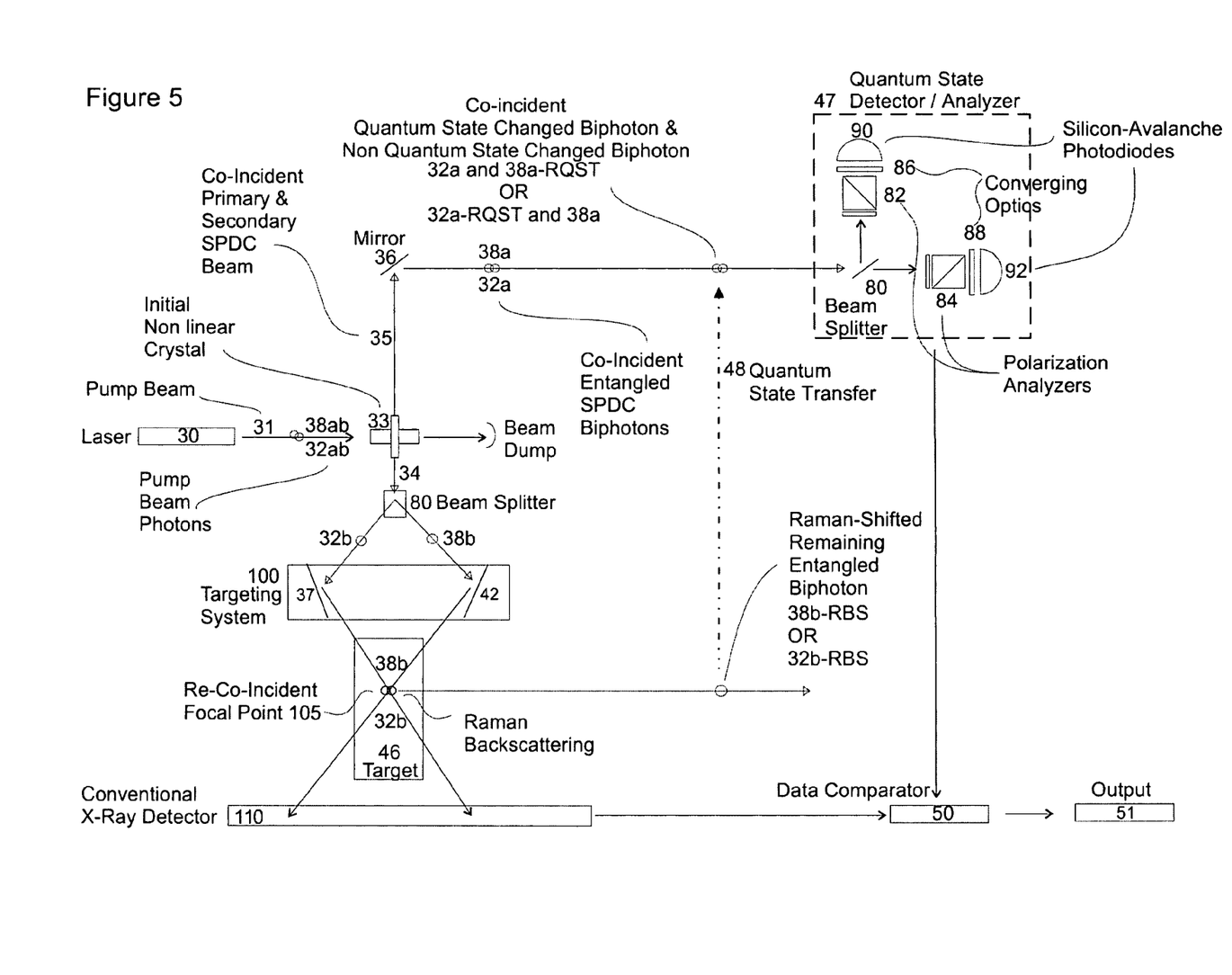
FIG. 5 shows a block diagram for performing Variable Penetration Depth Self-Referencing Raman Quantum State Transfer Spectroscopy.

FIG. 5 shows a block diagram illustrating how an apparatus having components similar to the apparatus of FIG. 3 in which both the geometry and optical paths of the beams have been adjusted to produce biphotons in the X-ray range. In this Figure, the crystal 33 produces two sets of biphotons represented by beams 34 and 35. The biphotons 32*b* and 38*b* forming beam 34 pass through a beam splitter (BS) 80 and into a targeting system (TS) 100. The targeting system (TS) 100 includes two mirrors 37, 42 that direct the two beams such that they cross each other within a target 46.

The targeting system TS 100 is also used to recombine photons 32*b* and 38*b* at a focal point (FP) 105 anywhere from the surface to deep inside the target 46 to induce Raman scattering. As discussed above the quantum changes in the entangled Raman backscatter photons will be transferred to the remote detector beam and then processed into the targets molecular makeup. By gradually moving the focal point through the target and sweeping the beam, a complete "full thickness" chemical determination of the target is possible along with its topographical image generated. Because not all the x-ray biphotons will interact with the target it is also possible to generate a conventional scan through the use of conventional x-ray detectors 110. This setup has applications for scanning luggage, cargo containers as well as medical CT scanners.

The Raman backscattered biphotons 32*b* 38*b* or corresponding biphotons 32*a*, 38*a* are analyzed by quantum state detector/analyzer 47 using the techniques described above, in conjunction with FIGS. 3 and 4. The results from each analysis can be processed separately, or can be compared using comparator 50 and a common output 51 may be generated providing information about target 46.

Figure 6:
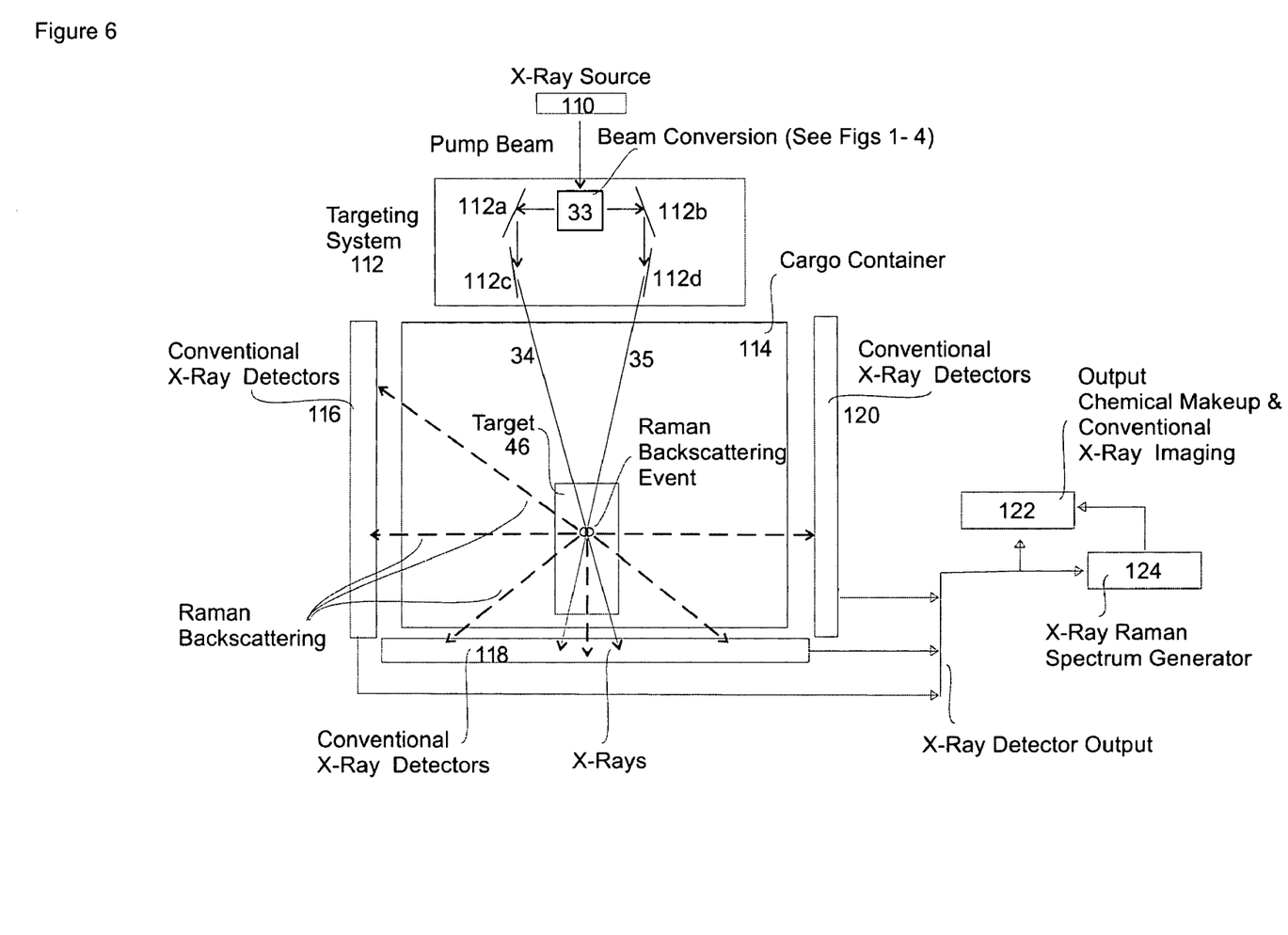
FIG. 6 shows a general block diagram for scanning a cargo container by using either conventional or coincident entangled hard X-rays to create Raman backscattering.

FIG. 6 demonstrates the general layout for scanning a cargo container by using either conventional or coincident entangled hard X-rays (using the apparatus of FIGS. 2, 3 or 5) to create Raman backscattering. More specifically, an X-ray pump beam from a source 110 is sent to a targeting system 112 that includes a beam conversion element 33 converting some of the photons into entangled beams of biphotons as discussed above. These beams are directed by a mirror system consisting of mirrors 112A-D into a relatively large target, such as a cargo container 114. The container 114 is positioned at a scanning station that includes a plurality of conventional X-ray detectors 116, 118, 120. The targeting system shifts the two beams around within the container 114 until all, or at least substantially all the interior volume of the container has been scanned.

The resultant X-rays are sensed by X-ray detectors 116, 118, 120 and the information collected by these scanners is fed to an output generator 122. In addition, a Raman backscatter detector 124 is also provided that detects the Raman backscatter from within the container 114. The output of detector 124 is also fed to generator 122. The output generator analyzes the information from the various detectors and then generates an output that includes 3D information of various articles within the container 114, as well as chemical (or biological) composition thereof.

Figure 7:
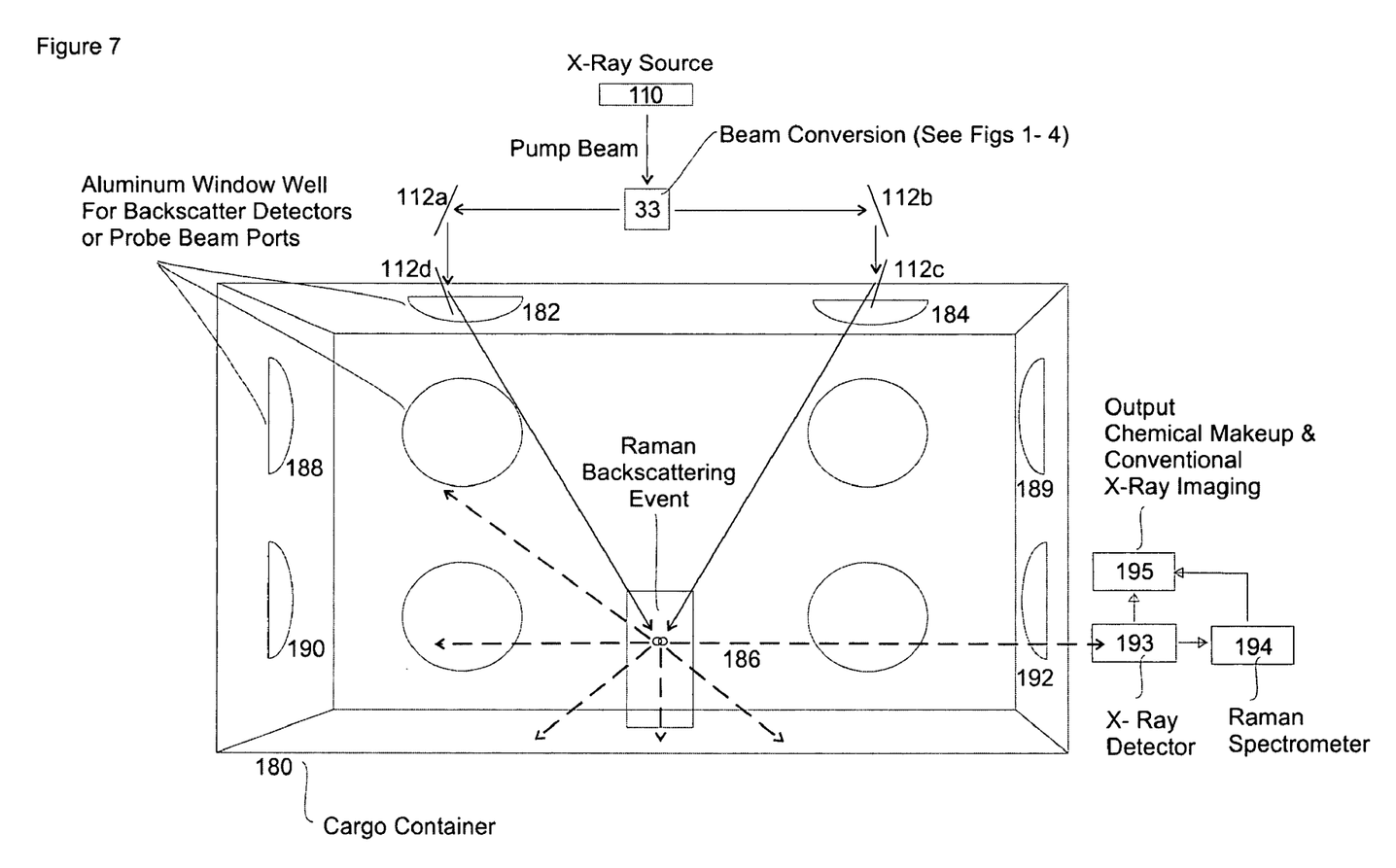
FIG. 7 shows a general block diagram for a device for scanning a cargo container by using either conventional or coincident entangled soft X-rays aimed through X-ray transparent ports to create Raman backscattering.

FIG. 7 demonstrates the general layout for scanning a cargo container by using either conventional or coincident entangled soft X-rays (FIGS. 2,3,5) aimed through access ports to create Raman backscattering. These ports are nothing more than a small depression in the wall of the cargo container consisting of X-ray transparent material, like plastic, glass or aluminum, in which the tip of a targeting system could be inserted. The advantage to this is that existing cargo containers could be easily retrofitted and the steel container itself could act as shielding. In this embodiment, a cargo container 180 includes two windows 182, 184 that may be on the same wall of the container or on different walls. Moreover, the windows 182, 184 could be disposed on the sidewalls, the roof, or the floor of the container. The two beams of X-rays and entangled biphotons enter through windows 182, 184 as shown and are directed toward a common zone 186 within the container 180. The zone 186 can be moved about as desired.

The beams collected from the zone 186 are captured by detectors through one of the windows 186-192. A Raman backscatter detector 194 is shown receiving a beam through window 192. Several detectors 194 could be provided, one for each window, or one or more detectors can be shifted around from one window to another. The detectors are used to generate an output as described above in conjunction with FIG. 6.

Figure 8:
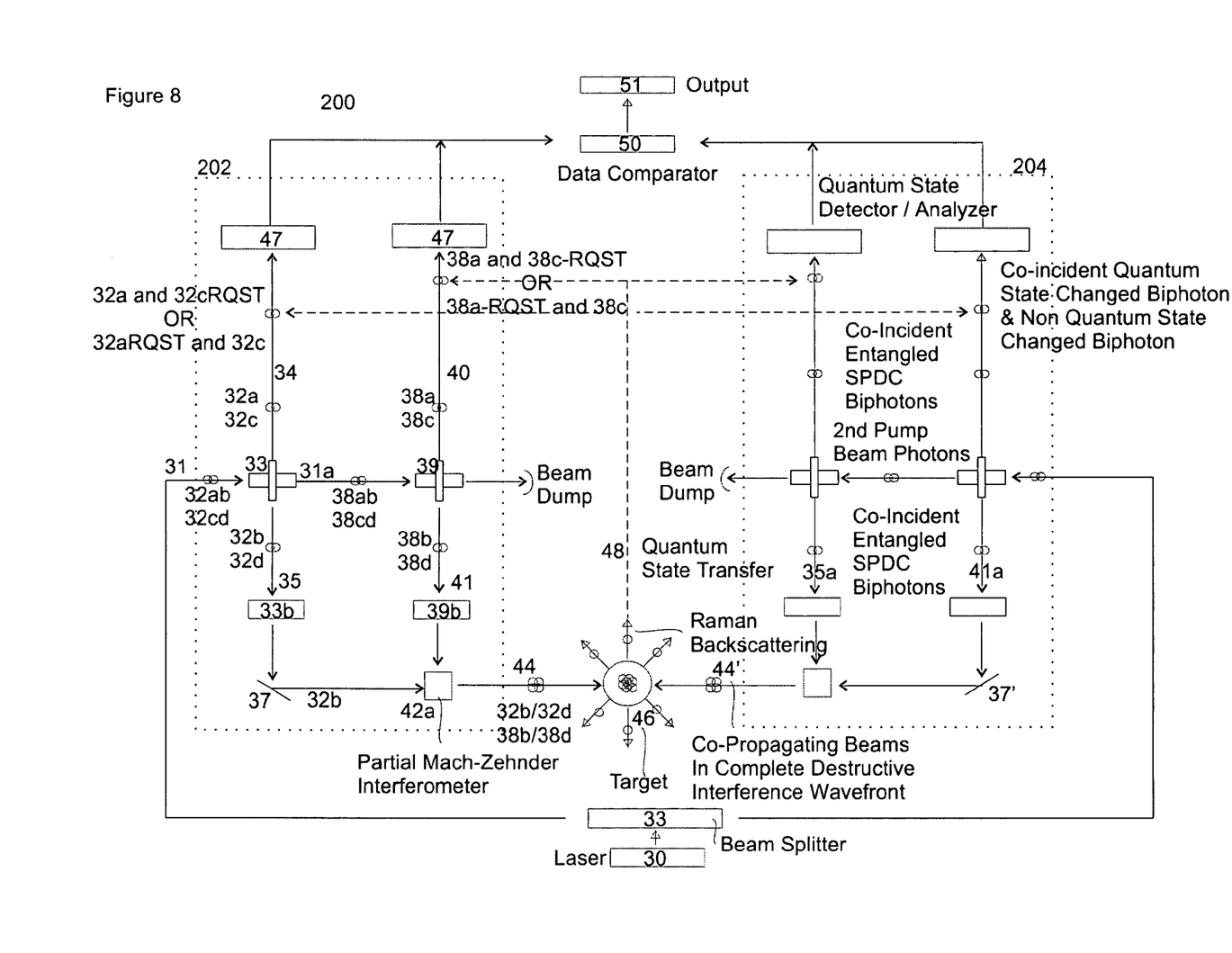
FIG. 8 shows a block diagram of performing Variable Penetration Depth Self-Referencing Raman Quantum State Transfer Spectroscopy utilizing non-ionizing frequencies.
Figure 9:
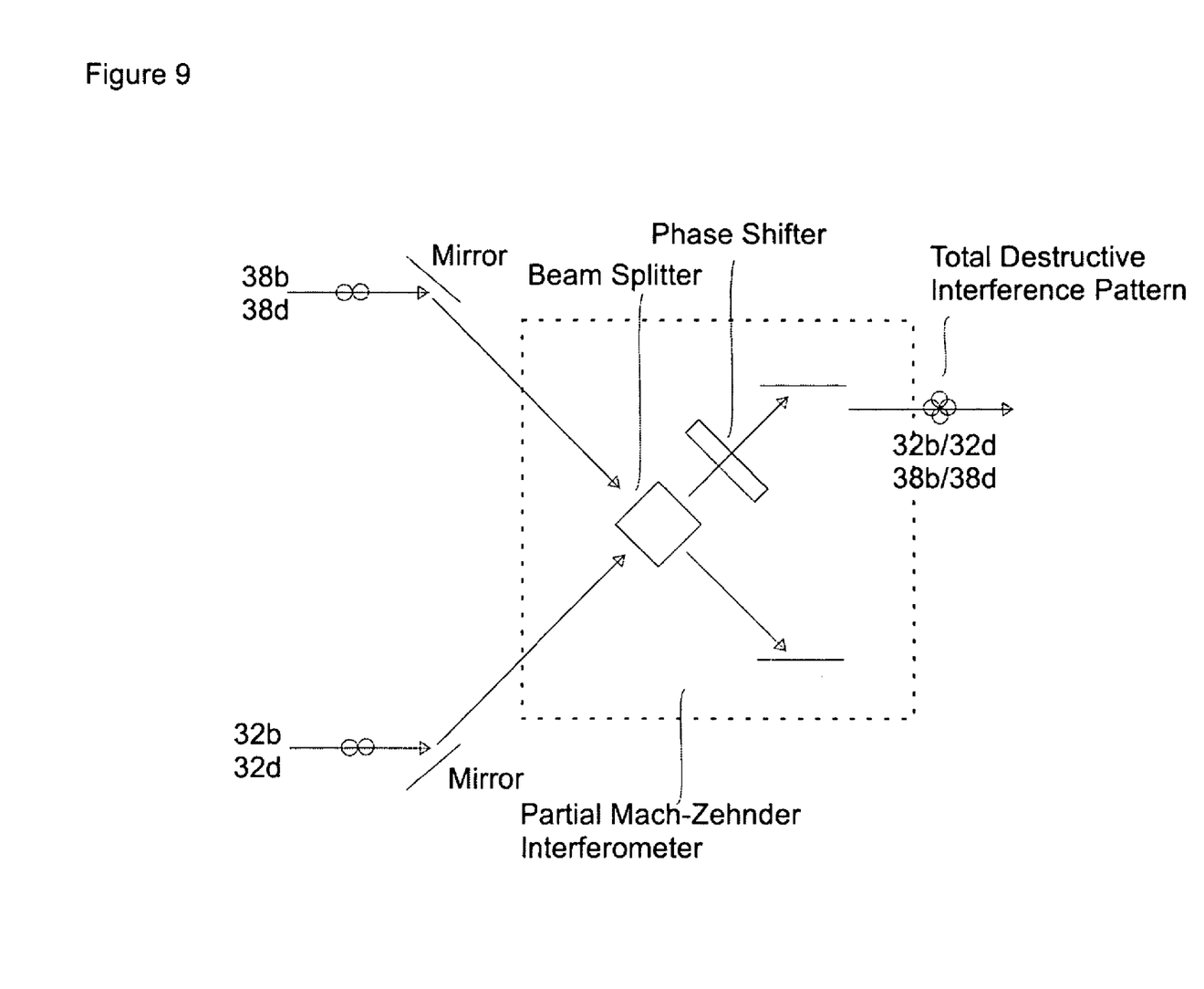
FIG. 9 shows a block diagram of a method used to place two separate pairs of Coincident Twin Entangled Biphoton in superposition.

FIG. 8 a block diagram of another embodiment. This embodiment shows an apparatus that is a hybrid of the configurations shown in FIGS. 2 and 3. More specifically, the embodiment 200 of FIG. 8 has the general layout of FIG. 2 but the photon production is implemented using the device of FIG. 3. The optical geometry of FIG. 8 places two of these hybrid systems 202, 204 set opposite to each other so that their respective target beams A and B will pass through one another as they are directed toward target 46. As shown in FIG. 8, the two systems 202 and 204 are essentially identical.

The difference in this configuration is beams 35 and 41 are set 180 degrees out of phase with each other so their amplitude and frequency are summed to zero. Beams 35a and 41a are similarly constructed. Since both opposing beams have had their frequency and amplitude displaced, or offset and therefore beam 44 consists only of an anti-node or "null carrier area" that propagates and it is therefore expected that it will not interact with matter. The same is true of beam 44'. As discussed above, beams 44, 44' consist of dual beams of entangled biphotons.

This technique enable biphotons generated in the infrared, visual or ultra-violet wavelengths to be penetrate solid matter, such as target 46 like X-rays. Once the "null carrier area" or node has entered the target it is necessary to get frequency and amplitude of the photons to re-emerge so they will effectively interact to yield Raman backscattering or just absorption. This is accomplished by generating beam 44' with a phase delay with respect to beam 44. The phase of the biphoton beams can be set by the characteristics of down-conversion crystals 33a, 33b, 39a, 39b or the path length or even through Acousto-Optical Tunable Filters 35, 35a, 41, 41a or a combination thereof. In any case the optical geometry is adjusted so that the phase of beam of 44' is out of sync with the phase of beam 44 by a predetermined angle. If this angle is chosen properly, (e.g. to an angle of 90 degrees) then as the two sets of opposing beams pass through each other inside the target 46, it is presently believed, wave summing of their phases would occur causing a momentary re-emergence of part of both the frequency and amplitude. This summing re-phases the photons with the vibrational modes of the target, allowing interaction at the "focal point" and thereby yielding Raman backscatter or absorption of photons. In order to create this "focal point" it is necessary to pulse both opposing beams at sufficiently short intervals that they only interact for several millimeters within the target and not along the entire optical path length. The backscatter spectra or absorption transmission spectrum could then be detected through quantum state transfer, (e.g. by processing the outputs of analyzers 47 and comparing the same with the comparator 50. The output may be dependent on the geometry of the system.

Obviously, this technique has numerous advantages over conventional penetrating scan methods because it does not require the use of any ionizing radiation. That means there is no deployment of radioactive isotope sources, no protective shielding is necessary for operators nor is there any concern over scanning targets or individuals for that matter. As in the design of FIG. 5, the technique of FIG. 8 also has applications for scanning luggage, cargo containers and medical scanners.

Numerous other modifications may be made to the invention without departing from its scope as defined in the appended claims.

I claim:

1. An apparatus for analyzing an object comprising:
    a laser generating an initial pump beam;
    a first nonlinear crystal receiving said initial pump beam and generating a second pump beam and first and second primary Spontaneous Parametric Downconversion (SPDC) beams;
    a second nonlinear crystal receiving said second pump beam and generating first and second secondary SPDC beams;
    polarizing means for adjusting a phase angle of at least some of said primary and secondary SPDC beams;
    first combining means for combining the first primary SPDC beam with the first secondary SPDC beam to form first coincident SPDC beams;
    second combining means for combining the second primary beam with the second secondary beam to form second coincident SPDC beams;
    means for directing the first coincident SPDC beams at an article;
    and
    means for analyzing Raman backscattering associated with the impingement of said first SPDC beams on said article to derive a predetermined characteristic of said article.

2. The apparatus of claim 1 wherein said means for analyzing includes a Raman backscatter sensor adapted to receive Raman backscatter from said article and to generate a Raman spectrum.

3. The apparatus of claim 2 further comprising comparing means comparing a Raman spectrum with the signatures of known components.

4. The apparatus of claim 1 wherein said analyzing means includes an analyzer receiving the second coincident SPDC beams to determine said predetermined characteristics.

5. The apparatus of claim 4 wherein said analyzing means further comprises a comparator for comparing said Raman backscattering of said comparator with the signature of a known component.

6. An apparatus for performing Raman analyses on an article comprising:
    a laser generating a pump beam;
    a non-linear crystal receiving said pump beam and generating two coincident Spontaneous Parametric Downconversion (SPDC) beams, each SPDC beam including a primary and a secondary beam;
    means for directing one of said coincident SPDC beams at the article; and
    analyzing means for analyzing one of said two coincident beams to determine a characteristic of said article, said analyzing means includes a beam splitter that splits said second coincident SPDC beam into two corresponding orthogonal beams and two sensors receiving said orthogonal beams, said sensors include polarization sensors that sense the polarization of the respective orthogonal beams.

7. The apparatus of claim 6 further including output means generating an output dependent on said polarization sensors.

8. The apparatus of claim 7 wherein said analyzing means further includes a Raman backscatter analyzer receiving Raman scatter photons from the article.

9. The apparatus of claim 8 further comprising a comparator receiving an output from said analyzing means and comparing the same to sample signatures.

10. The apparatus of claim 6 further comprising means for directing said primary and secondary beams at a target.

11. The apparatus of claim 10 wherein said beams are directed by said directing means at a predetermined angle into said article.

12. The apparatus of claim 10 further comprising targeting means for directing said beams to be coincident at different locations within the article.

13. The apparatus of claim 10 further comprising an X-ray detector positioned to detect X-rays resulting from said beams.

14. The apparatus of claim 6 wherein said pump beam is generated by an X-ray source.

15. The apparatus of claim 14 wherein said analyzing means includes a Raman backscatter analyzer intercepting and analyzing Raman backscatter particles and an X-ray detector analyzing X-ray particles.

16. The apparatus of claim 15 wherein said article is a container having a plurality of apertures oriented to either receive external beams and distribute them within the container, or outgoing beams that are directed to respective sensor.

17. An apparatus for analyzing an article comprising:
a generator generating first and second coincident Spontaneous Parametric Downconversion (SPDC) beams;
a reflector directing said coincident SPDC beams at a target; and
an analyzer analyzing the resulting Raman backscatter to determine a characteristic of said target.

18. An apparatus for analyzing an article comprising:
means for generating a first set of Spontaneous Parametric Downconversion (SPDC) coincident beams and a second set of coincident SPDC beams, each set of coincident beams including a first beam and a second beam, said first and second beams being out of phase by 180 degrees; and
means for directing the two sets of beams at the article from different angles to cause the first and second set of beams to intersect within the article.

19. The apparatus of claim 18 wherein said first and second set of beams are out of phase by a predetermined angle from each other.

20. The apparatus of claim 19 wherein said first and second set of beams are offset by about 90 degrees.

* * * * *